(12) United States Patent
Kobayashi et al.

(10) Patent No.: US 8,662,361 B2
(45) Date of Patent: Mar. 4, 2014

(54) LIQUID DISCHARGING DEVICE, LIQUID DISCHARGING CARTRIDGE, AND DEVICE BODY CAP

(75) Inventors: Masaya Kobayashi, Yokohama (JP); Hideki Kaneko, Yokohama (JP); Masaru Sugita, Tokyo (JP); Masahiro Takei, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 999 days.

(21) Appl. No.: 12/613,447

(22) Filed: Nov. 5, 2009

(65) Prior Publication Data
US 2010/0116269 A1    May 13, 2010

(30) Foreign Application Priority Data

Nov. 7, 2008  (JP) ................................. 2008-286729

(51) Int. Cl.
*B65D 47/00* (2006.01)
*B67D 3/00* (2006.01)

(52) U.S. Cl.
USPC ........................................................ 222/562

(58) Field of Classification Search
USPC ................. 222/562, 129, 183, 182, 131, 225, 222/DIG. 1; 220/254.1, 254.5, 254.7; 215/264–265, 267
See application file for complete search history.

(56) References Cited

U.S. PATENT DOCUMENTS 4,185,756 A * 1/1980 Sciamonte .................... 222/83.5

FOREIGN PATENT DOCUMENTS

| EP | 861732 | 9/1998 |
|---|---|---|
| JP | 2001-277529 | 10/2001 |
| JP | 2004-283244 A | 10/2004 |
| JP | 2007-296384 | 11/2007 |
| WO | WO03/068513 | 8/2003 |

* cited by examiner

*Primary Examiner* — Paul R Durand
*Assistant Examiner* — Vishal Pancholi
(74) *Attorney, Agent, or Firm* — Canon USA Inc IP Division

(57) ABSTRACT

A liquid discharging device includes a device body configured to house a liquid discharging cartridge body having a liquid discharging portion for discharge liquid, and a device body cap removably attached to the device body. When the device body cap is detached from the device body, a discharging portion cap attached to the liquid discharging cartridge body so as to protect a discharging port of the liquid discharging portion is detached from the liquid discharging portion in combination with the device body cap.

9 Claims, 23 Drawing Sheets

FIG. 14A  FIG. 14B  FIG. 14C
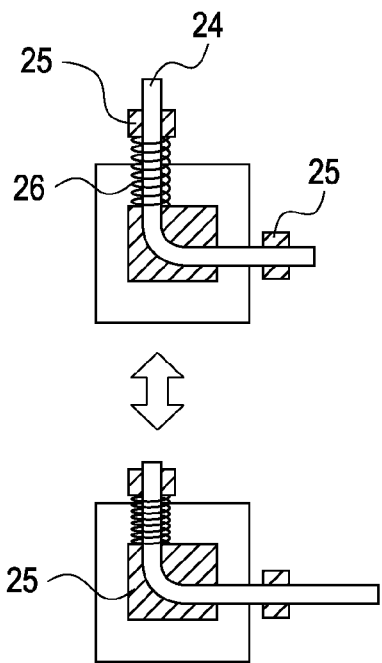
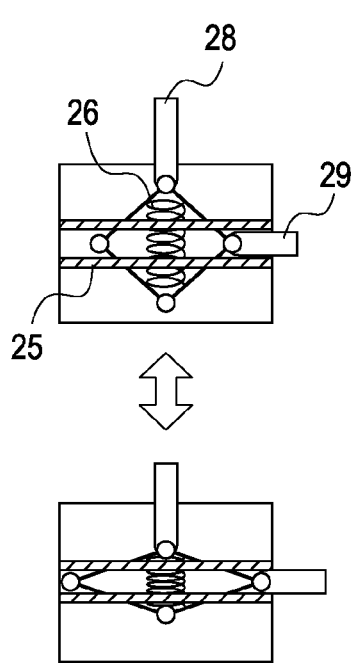
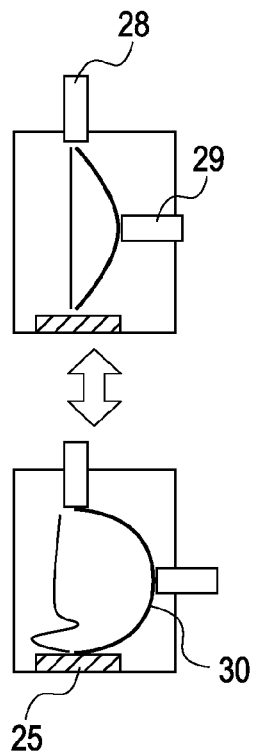
FIG. 14D  FIG. 14E
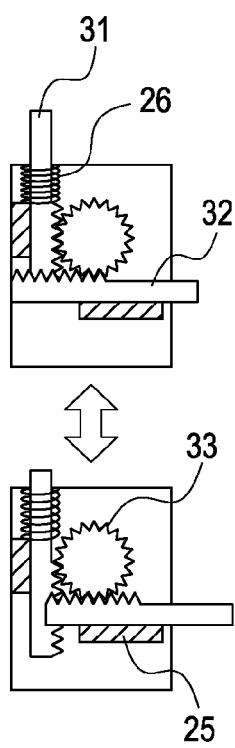
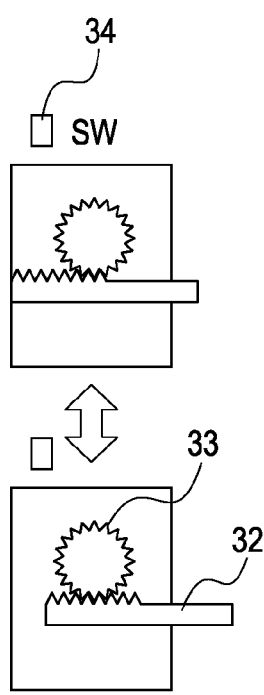

LIQUID DISCHARGING DEVICE, LIQUID DISCHARGING CARTRIDGE, AND DEVICE BODY CAP

BACKGROUND OF THE INVENTION

1. Field of the Invention

The present invention relates to a liquid discharging device, a liquid discharging cartridge to be contained in the liquid discharging device, and a device body cap removably mounted on a main body of the liquid discharging device.

2. Description of the Related Art

Liquid discharging devices that help the user to inhale liquid medicine have been developed. The liquid-medicine discharging devices discharge the liquid medicine in the form of minute droplets into an air passage, through which air sucked via a mouthpiece flows, by utilizing the discharging principle of an inkjet method. In an example of such a liquid discharging device, a liquid discharging cartridge is replaceable. The liquid discharging cartridge basically includes a liquid discharging cartridge body and a discharging portion cap for protecting a liquid discharging portion of the liquid discharging cartridge (see Japanese Patent Laid-Open No. 2007-296384).

Such a discharging portion cap is detached when the liquid discharging cartridge is mounted in the body of the liquid discharging device. This causes a problem of convenience, for example, detachment is troublesome.

SUMMARY OF THE INVENTION

The present invention provides a unit that allows a discharging portion cap of a liquid discharging cartridge to be detached easily.

A liquid discharging device according to a first aspect of the present invention includes a device body configured to house a liquid discharging cartridge body having a liquid discharging portion that discharges liquid; a device body cap removably attached to the device body; and a coupling member configured to couple the device body cap to a discharging portion cap attached to the liquid discharging cartridge body so as to protect a discharging port of the liquid discharging portion. The coupling member causes the discharging portion cap to be detached from the liquid discharging portion cap when the device body cap is detached from the device body.

A liquid discharging cartridge according to a second aspect of the present invention includes a liquid discharging portion configured to discharge liquid; and a discharging portion cap configured to protect a discharging port of the liquid discharging portion. The discharging portion cap includes a coupling member to be coupled to a device body cap provided in a device body of a liquid discharging device that houses the liquid discharging cartridge. The coupling member causes the discharging portion cap to be detached from the liquid discharging portion when the device body cap is detached from the device body.

A device body cap according to a third aspect of the present invention is removably attached to a device body of a liquid discharging device that houses a liquid discharging cartridge body having a liquid discharging portion for discharging liquid. The device body cap includes a coupling member to be coupled to a discharging portion cap provided in the liquid discharging cartridge body so as to protect a discharging port of the liquid discharging portion. The coupling member causes the discharging portion cap to be detached from the liquid discharging portion when the device body cap is detached from the device body.

Further features of the present invention will become apparent from the following description of exemplary embodiments with reference to the attached drawings.

BRIEF DESCRIPTION OF THE DRAWINGS

FIGS. 14A to 14E are schematic views showing members for unfixing the discharging head cap by changing the direction of force.

DESCRIPTION OF THE EMBODIMENTS

Figure 1A:
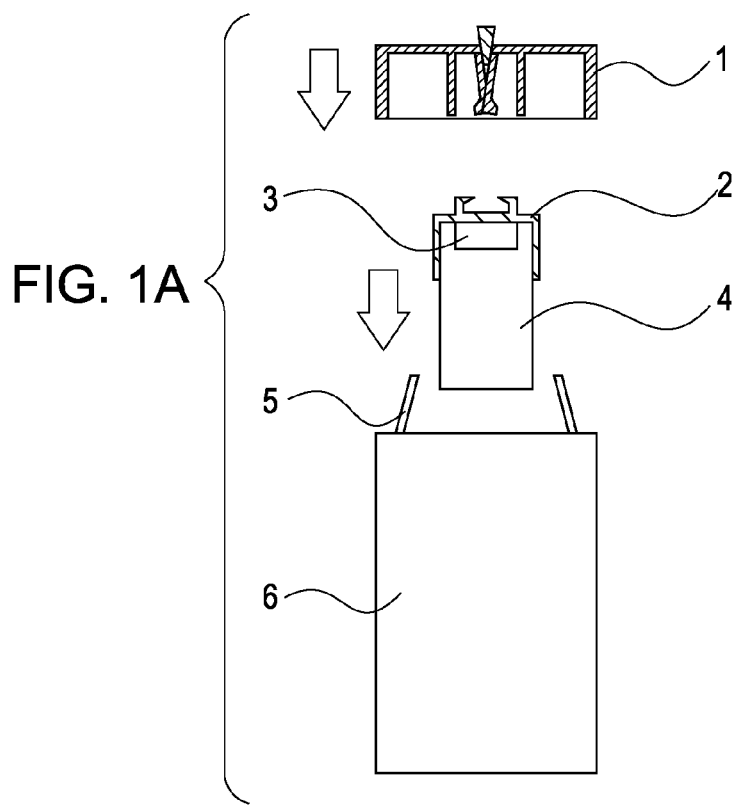
FIGS. 1A to 1C are schematic views showing a conceptual configuration of a liquid discharging device according to an embodiment of the present invention.

The present invention will be described in more detail below with reference to the drawings. In principle, like components are denoted by like reference numerals, and descriptions thereof are omitted.

Figure 1B:
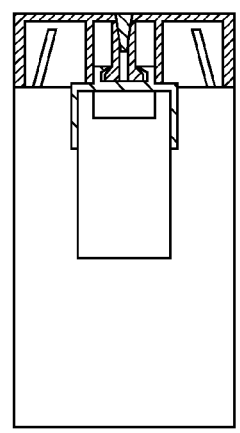
Figure 1C:
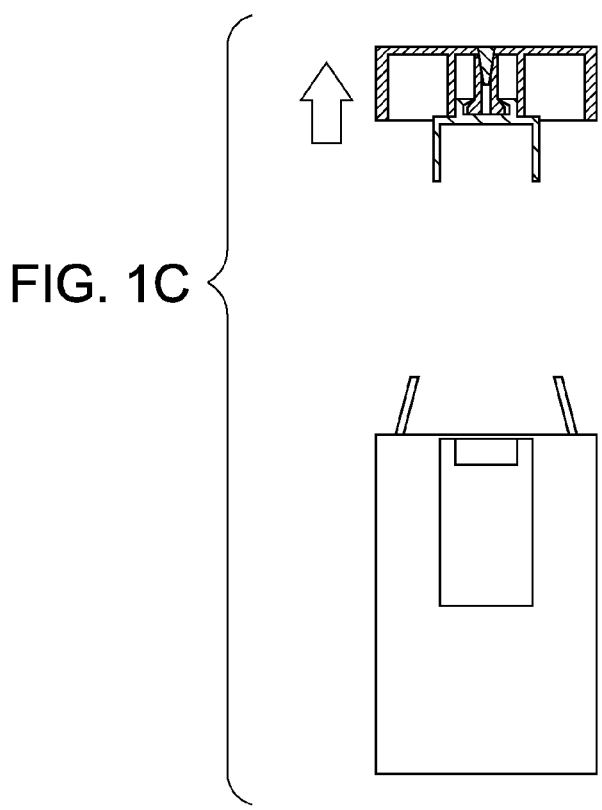

FIGS. 1A to 1C are schematic views showing the configuration of a liquid discharging device according to an embodiment of the present invention. In this embodiment, a description will be given of a liquid discharging device for medicine inhalation, which allows medicine serving as liquid stored in a liquid discharging cartridge to be inhaled through a mouthpiece. A liquid discharging device includes a liquid discharging cartridge body 4 having a discharging head 3 serving as a liquid discharging portion for discharging liquid, and a discharging head cap (discharging portion cap) 2 for covering the discharging head 3. The discharging head cap 2 aims to protect discharging ports of the discharging head 3 so that dust will not adhere to the discharging ports and so that the surfaces of the discharging ports will not be scratched by touch, or to retain moisture so that the viscosity of liquid in the discharging ports will not change or the liquid will not dry. A liquid discharging device to which the present invention is applicable includes the liquid discharging cartridge, a device body 6 housing the liquid discharging cartridge, and a device body cap 1 covering the device body 6.

In the present invention, the device body cap 1 is defined as a cap that is removably attached to the device body 6, that is, a cap that is detached when the device is used and is attached when the device is not used. Preferably, the device body cap 1 covers the device body 6 to cut off the interior of the device body 6 from external air so that dust will not enter the device body 6 when the liquid discharging cartridge is not mounted. Further preferably, when a mouthpiece 5 is attached to the device body 6, the device body cap 1 also covers and protects the mouthpiece 5.

When using the liquid discharging device, the user detaches the device body cap 1, and attaches the liquid discharging cartridge to the device body 6 (FIG. 1A). Then, the user attaches the device body cap 1 to the device body 6 to combine the device body cap 1 with the discharging head cap 2 (FIG. 1B). When the user detaches the device body cap 1 from the device body 6, the discharging head cap 2 is detached in combination with the device body cap 1 (FIG. 1C). Then, the user inhales the medicine while holding the mouthpiece 5 in the user's mouth.

The mouthpiece 5 can be replaced with a nosepiece (not shown) according to the application. The user can inhale the medicine from the nose with the nosepiece held in the mouth.

While medicine is used as the liquid in the embodiment, the liquid of the present invention is not limited to medicine, and may be liquid perfume or liquid pigment.

As a device for discharging liquid, a device that generates energy for discharging pressurized gas or liquid can be adopted. While an arbitrary discharging energy generating element may be used, for example, an electrothermal transducer for applying heat energy to the liquid or an electromechanical transducer for applying mechanical energy to the liquid can be used. That is, for example, the liquid can be discharged by a method of discharging droplets of liquid from discharging ports by applying heat energy to the liquid with an electrothermal transducer (thermal jet method), a method of discharging droplets of liquid from the discharging ports by using vibratory pressure of an electromechanical transducer (e.g., a piezoelectric element) for applying mechanical energy to the liquid (piezo-jet method), or a method of discharging minute droplets of liquid by generating fine bubbles in the liquid by ultrasound and using recoil force produced when the minute bubbles burst on the liquid surface (ultrasonic mist method). A method of forming droplets can be arbitrary selected in accordance with the type of liquid.

When a thermal jet method is used, it is possible, in each discharging head, to increase the bore diameter of the discharging ports, the amount of pulse heat energy used for discharging, size accuracy of mircoheaters serving as electrothermal transducer, and reproducibility. For this reason, a narrow droplet diameter distribution can be achieved. Further, since the production cost of the head is low, the thermal jet method is highly applicable to small devices in which the head needs to be frequently replaced. Hence, it is particularly preferable to adopt the discharging principle of the thermal jet method in an application to a liquid discharging device that requires portability and convenience.

Combination of Device Body Cap and Discharging Head Cap

Figure 2A:
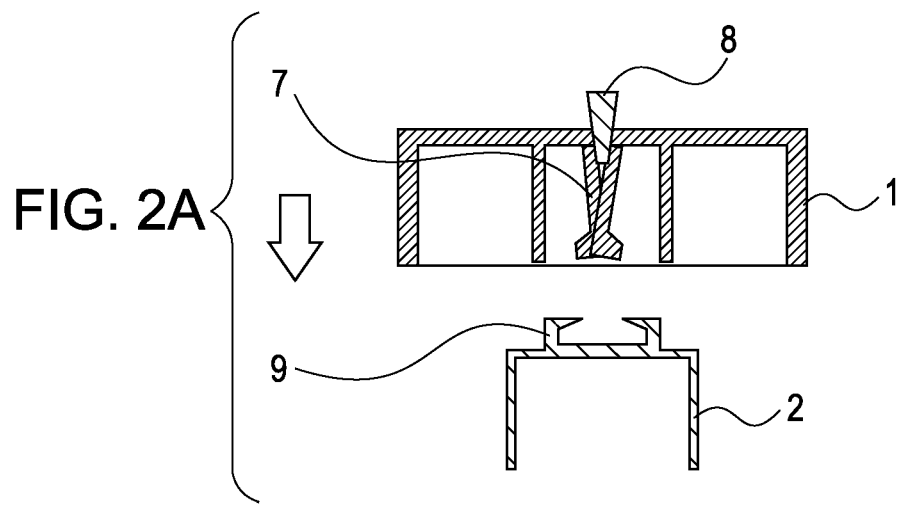
FIGS. 2A and 2B are cross-sectional views showing a member for combining a device body cap and a discharging head cap with a hook.
Figure 2B:
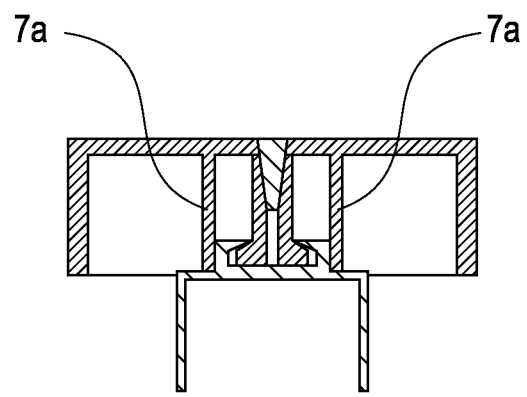

FIGS. 2, 3, and 4 show units for combining a device body cap 1 and a discharging head cap 2. FIGS. 2A and 2B are cross-sectional views of a first example of a combining unit. FIG. 2A shows a state in which the device body cap 1 and the discharging head cap 2 are not combined, and FIG. 2B shows a state in which the device body cap 1 and the discharging head cap 2 are combined. The discharging head cap 2 is provided with a fixed hook portion 9, and the device body cap 1 is provided with a movable hook portion 7 serving as a coupling member to be coupled to the discharging head cap 2. The movable cap portion 7 has a combination operating member 8 serving as a switch member for switching between states in which the device body cap 1 and the discharging head cap 2 are combined and not combined. By pushing down the combination operating member 8, the movable cap portion 7 opens outward to be coupled to the fixed hook portion 9.

Preferably, the combination operating member 8 protrudes out before the device body cap 1 and the discharging head cap 2 are combined, and is flush with or slightly recedes from the surface of the device body cap 1 after the device body cap 1 and the discharging head cap 2 are combined. This aims to prevent the user from making a human mistake of erroneously pushing the combination operating member 8 after combination. Preferably, like a knock-type ballpoint pen, the combination operating member 8 incorporates a spring (not shown) such that the movable cap portion 7 is opened by pushing the combination operating member 8 once and is closed by pushing the combination operating member 8 again. This is because the discharging head cap 2 is attached again to the liquid discharging cartridge body 4 when the liquid discharging cartridge body 4 is removed. When movable hook portion guides 7a are provided in the device body cap 1 in a manner such as to cover the fixed hook portion 9, stability is improved.

Figure 3A:
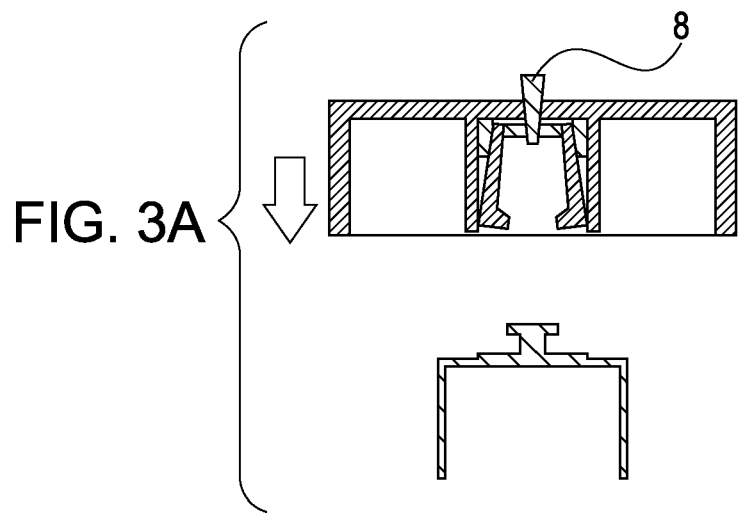
FIGS. 3A and 3B are cross-sectional views showing another member for combining a device body cap and a discharging head cap with a hook.
Figure 3B:
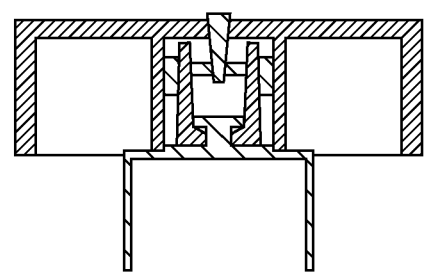

FIGS. 3A and 3B are cross-sectional views showing a second example of a unit for combining a movable hook portion and a fixed hook portion in which the movable hook portion reversely moves to close from the outer side to the inner side. FIGS. 3A shows a state before combination, and FIG. 3B shows a state after combination.

Figure 4A:
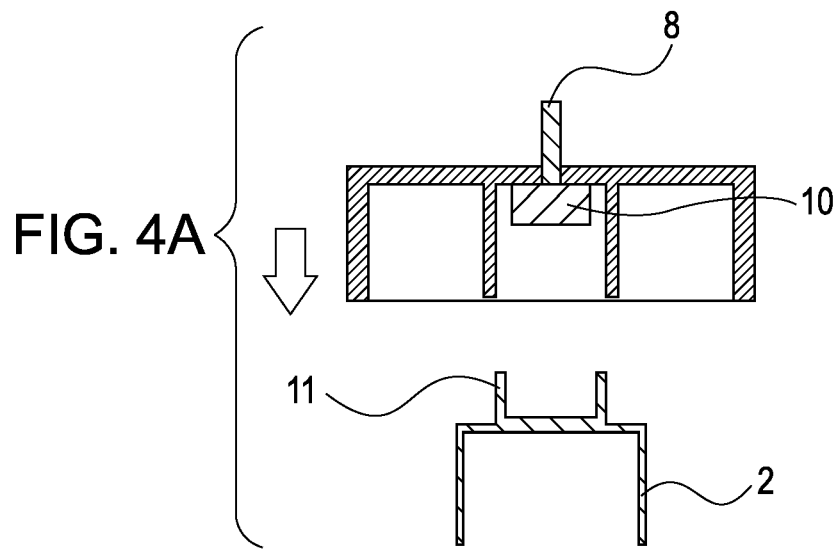
FIGS. 4A and 4B are cross-sectional views showing a further member for combining a device body cap and a discharging head cap with a magnet.
Figure 4B:
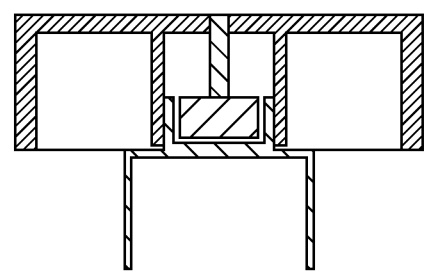

FIGS. 4A and 4B are cross-sectional views showing a third example of a unit for combining the device body cap 1 and the discharging head cap 2 by using a magnet. FIG. 4A shows a state before combination, and FIG. 4B shows a state after combination. The discharging head cap 2 has a magnet attraction member 11. The device body cap 1 includes a magnet 10 serving as a coupling member for coupling to the discharging head cap 2, and a combination operating member 8 serving as a switch member. The user pushes down the combination operating member 8 so as to bring the magnet 10 into contact with the magnet attracting member 11.

Fixing of Discharging Head Cap to Liquid Discharging Cartridge Body

To prevent the user from erroneously removing a discharging head cap 2 from a liquid discharging cartridge body 4, the discharging head cap 2 is preferably provided with a discharging-head-cap fixing member for fixing to the liquid discharging cartridge body 4.

Figure 5A:
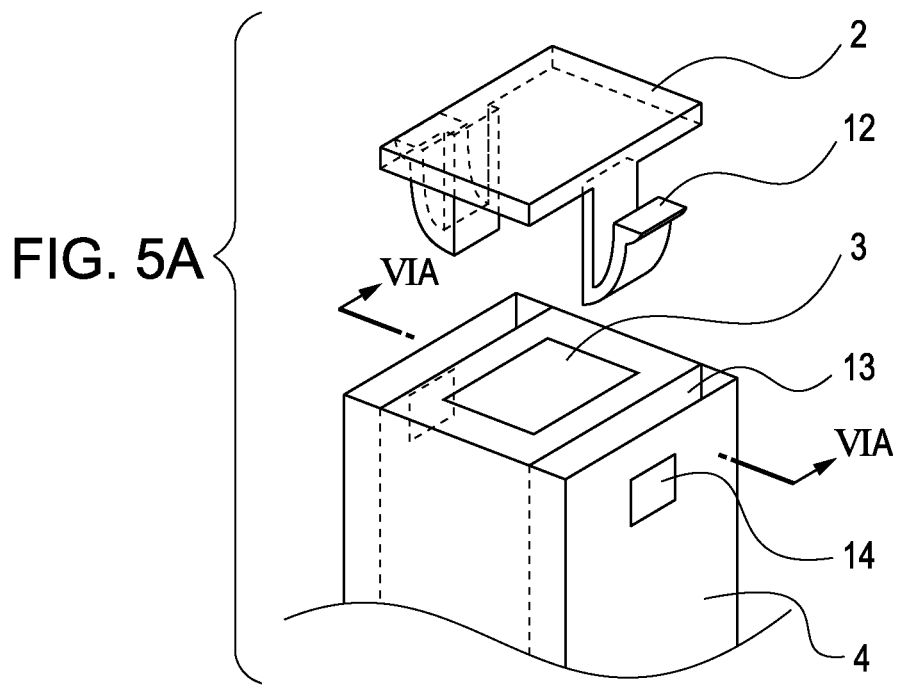
FIGS. 5A and 5B are perspective views showing discharging-head-cap fixing members using hooks.
Figure 5B:
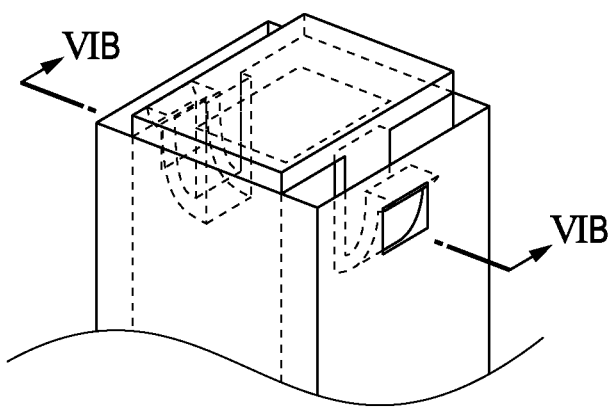

FIGS. 5A and 5B are perspective views showing a first example of a discharging-head-cap fixing member using hooks. FIG. 5A shows a state in which the discharging head cap 2 is not fixed, and FIG. 5B shows a state in which the discharging head cap 2 is fixed.

Figure 6A:
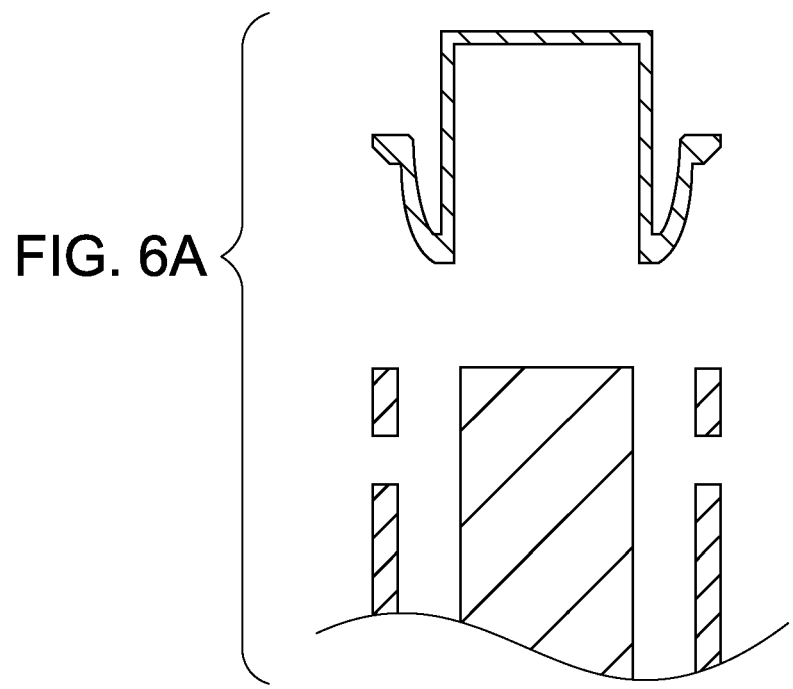
FIGS. 6A and 6B are cross-sectional views showing the discharging-head-cap fixing members shown in FIGS. 5A and 5B.
Figure 6B:
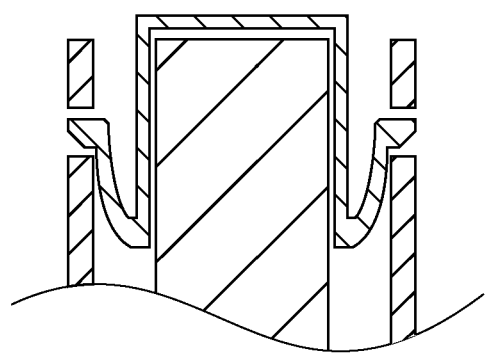

FIGS. 6A and 6B are cross-sectional views, respectively, taken along line VIA-VIA of FIG. 5A and line VIB-VIB of FIG. 5B. The discharging head cap 2 has fixing hooks 12 serving as discharging-head-cap fixing members. The fixing hooks 12 are opened at apertures 14 through fixing-hook slits 13, and the discharging head cap 2 is thereby fixed to the liquid discharging cartridge body 4. To prevent the user from erroneously removing the discharging head cap 2 from the liquid discharging cartridge body 4, it is preferable to form a plurality of (two in FIGS. 5A and 5B) fixing hooks 12.

Figure 7A:
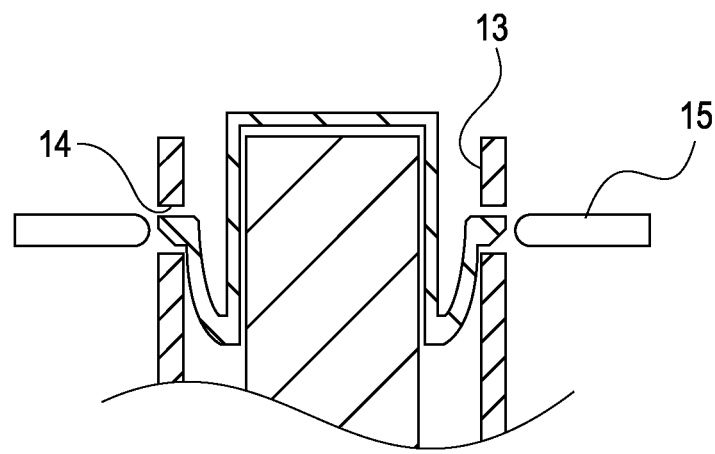
FIGS. 7A and 7B are cross-sectional views showing discharging-head-cap releasing members using hooks.
Figure 7B:
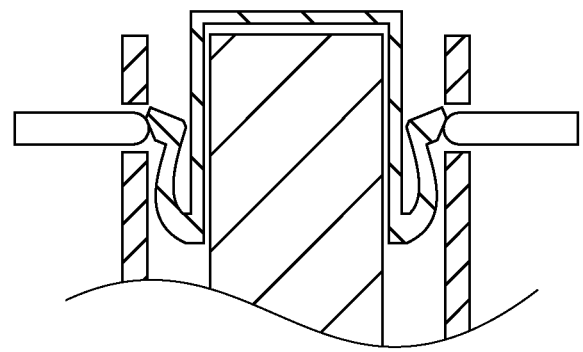

FIGS. 7A and 7B are cross-sectional views showing a member for unfixing the discharging head cap 2 from the hooks 12. FIG. 7A shows a state in which the discharging head cap 2 is fixed to the liquid discharging cartridge body 4, and FIG. 7B shows a state in which the discharging head cap 2 is unfixed.

By pushing a hook releasing member 15 serving as a discharging-head-cap releasing member for unfixing the discharging head cap 2 from the liquid discharging cartridge body 4 into the liquid discharging cartridge body 4, the fixing hooks 12 are compressed into the fixing-hook slits 13, whereby the discharging head cap 2 is unfixed.

Figure 8A:
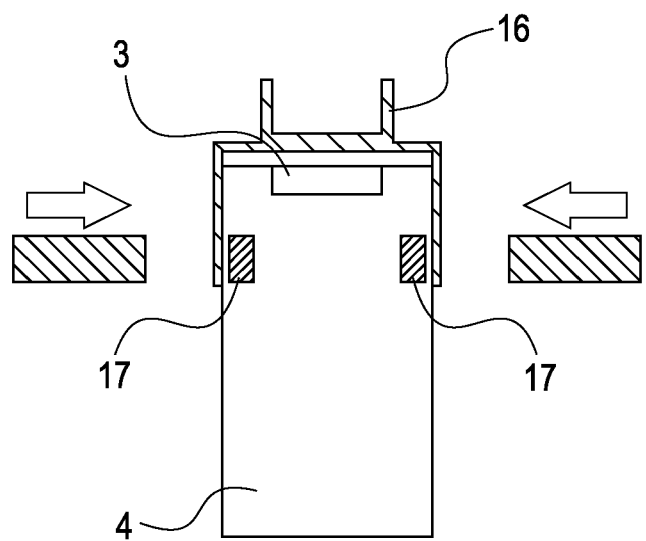
FIGS. 8A and 8B are cross-sectional views showing discharging-head-cap fixing and releasing members using magnets.
Figure 8B:
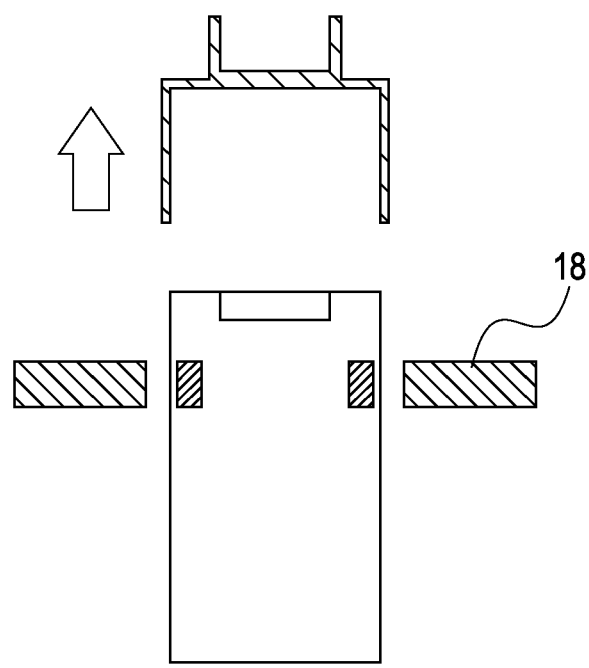

FIGS. 8A and 8B are cross-sectional views showing a second example of a discharging-head-cap fixing member using magnets, and a releasing member therefor. FIG. 8A shows a state in which the discharging head cap 2 is fixed, and FIG. 8B shows a state in which the discharging head cap 2 is unfixed. A plurality of magnets 17 are provided in the liquid discharging cartridge body 4, and are arranged in a manner such that the same polarities are located on outer sides. As shown in FIG. 8A, a discharging head cap 16 including a magnet attraction member is attracted by the magnets 17 and thereby protects the surface of the discharging head 3. To unfix the discharging head cap 16, as shown in FIG. 8B, discharging-head-cap releasing magnets 18 serving as discharging-head-cap releasing members are moved closer to the magnets 17. Polarities on the inner sides of the discharging-head-cap releasing magnets 18 are the same as polarities on the outer sides of the magnets 17. When the same polarities come closer to each other, the magnetic force of the magnets 17 decreases, and the attracting force of the discharging head cap 16 including the magnet attraction member decreases. This allows the discharging head cap 2 to be detached easily.

Figure 9A:
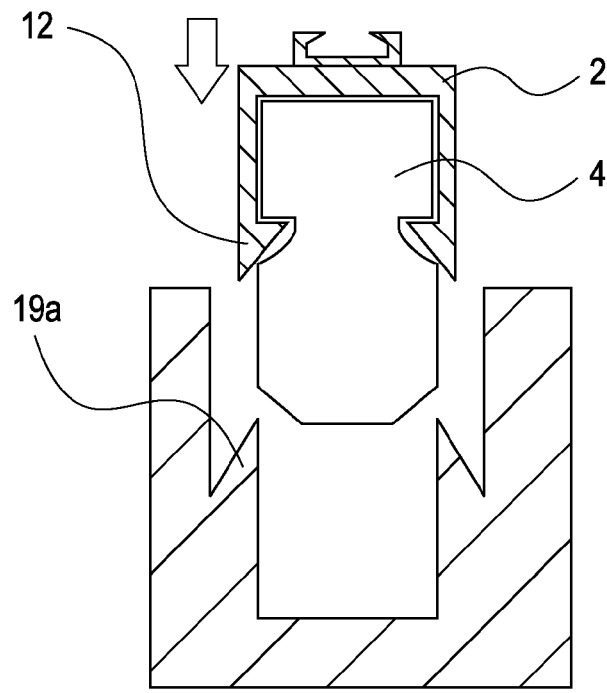
FIGS. 9A and 9B are cross-sectional views showing discharging-head-cap fixing and releasing members using inward hooks.
Figure 9B:
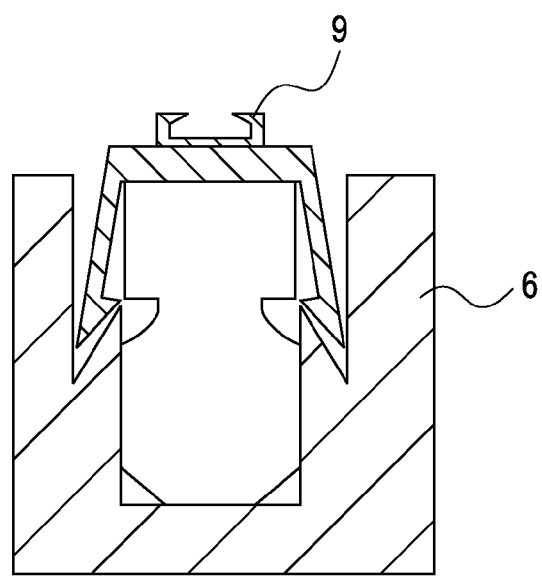

FIGS. 9A and 9B are cross-sectional views showing a third example of a discharging-head-cap fixing member using internal hooks, and a releasing member therefor. FIG. 9A shows a state in which the discharging head cap 2 is fixed, and FIG. 9B shows a state in which the discharging head cap 2 is unfixed. The device body 6 is provided with discharging-head-cap releasing members 19a having no movable portion. When the user attaches the discharging cartridge to the device body 6, the discharging-head-cap releasing members 19a push fixing hooks 12 open, so that the discharging head cap 2 is unfixed. When the user attaches the device body cap 1 to the device body 6 in this state so as to operate the combination operating member (switch member for switching between a state in which the device body cap 1 and the discharging head cap 2 are coupled and a state in which the caps are not coupled), the discharging head cap 2 can be detached in combination with the device body cap 1.

Combination of Device Body Cap and Discharging Head Cap

Figure 10A:
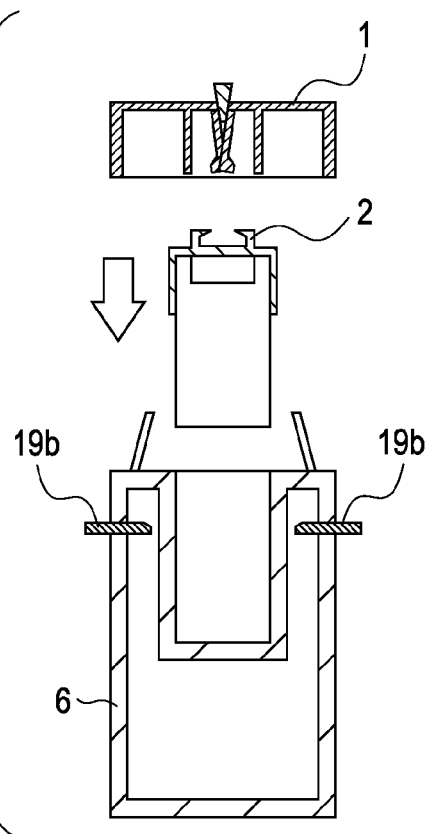
FIGS. 10A to 10E are cross-sectional views showing discharging-head-cap releasing members provided in a device body, and a series of operations thereof.
Figure 10B:
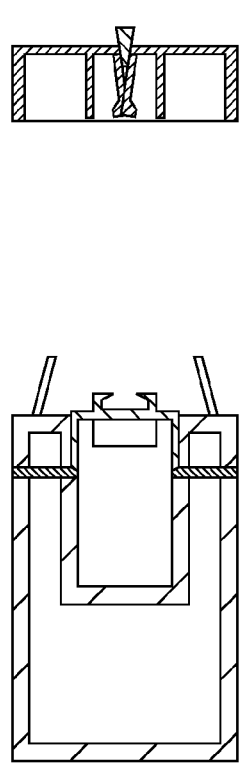
Figure 10C:
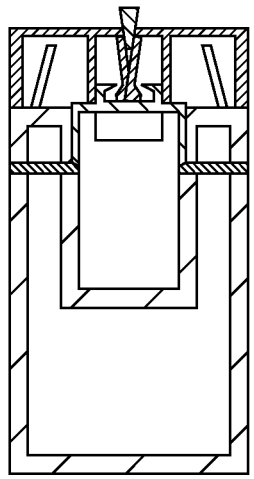
Figure 10D:
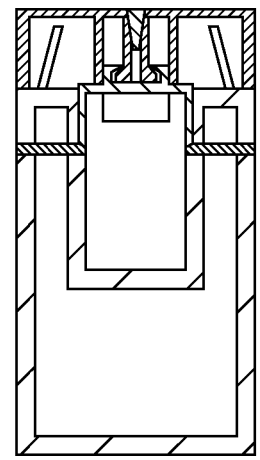
Figure 10E:
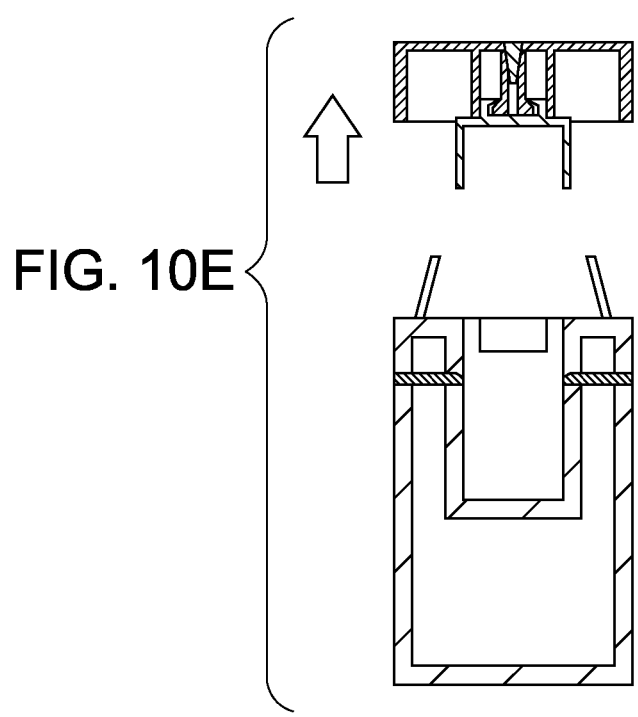

FIGS. 10A to 10E are cross-sectional views showing discharging-head-cap releasing members 19b for unfixing a liquid discharging cartridge body and a discharging head cap, and a series of operations. FIG. 10A shows a state in which a liquid discharging cartridge is placed outside a device body 6 before the discharging-head-cap releasing members 19b operate. FIG. 10B shows a state in which the liquid discharging cartridge is attached to the device body 6, and the discharging-head-cap releasing members 19b operate to unfix a discharging head cap 2. FIG. 10C shows a state in which a device body cap 1 is attached to the device body 6. FIG. 10D shows a state in which the device body cap 1 and the discharging head cap 2 are combined. FIG. 10E shows a state in which the combination of the device body cap 1 and the discharging head cap 2 is detached from the device body 6.

As shown in FIG. 10A, the discharging-head-cap releasing members 19b protrude from the device body 6 before operation. This aims to caution the user that liquid discharging is not ready. By pushing the discharging-head-cap releasing members 19b after attaching the liquid discharging cartridge, the discharging head cap 2 is unfixed, as shown in FIG. 10B.

Preferably, the time at which the discharging head cap 2 is unfixed is earlier than the time at which the device body cap 1 and the discharging head cap 2 are combined. This is because, in a case in which the combining time is earlier than the unfixing time, if an attempt is made to detach the device body cap 1 without performing unfixing, load is applied to the discharging head cap 2. When the device body 6 is electrically controlled, such failure can be avoided by using a sensor. Alternatively, after a series of operations are sequentially performed and the device body cap 1 becomes ready to be detached, this state may be indicated to the user with sound and light. Further alternatively, it is possible to produce a program that permits liquid discharging when a sensor detects that the discharging head cap 2 has been separated from the discharging head 3.

To remove the liquid discharging cartridge from the device body 6 after use, the steps shown in FIGS. 10E, 10D, 10C, 10B, and 10A are performed in that order. In this case, the user can properly and easily use the liquid discharging device without awareness of the discharging head cap 2 from the start of use to the end of use.

Fixing of Liquid Discharging Cartridge Body to Device Body

Figure 11A:
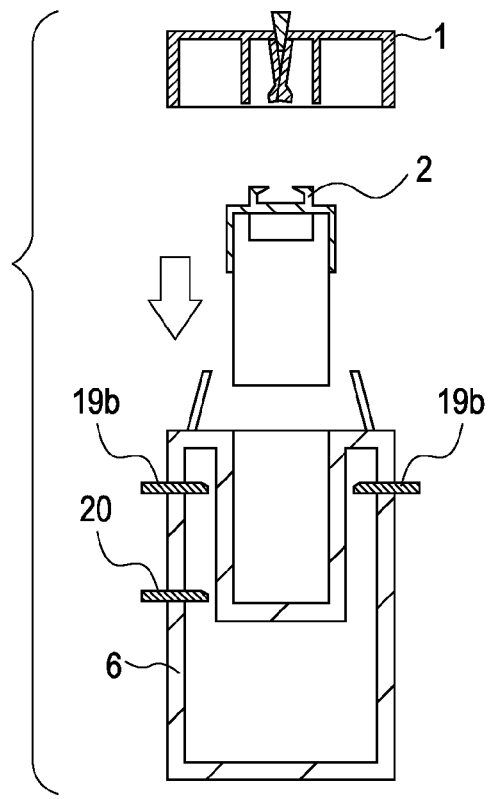
FIGS. 11A and 11B are cross-sectional views showing a liquid-discharging-cartridge fixing member provided in a device body.
Figure 11B:
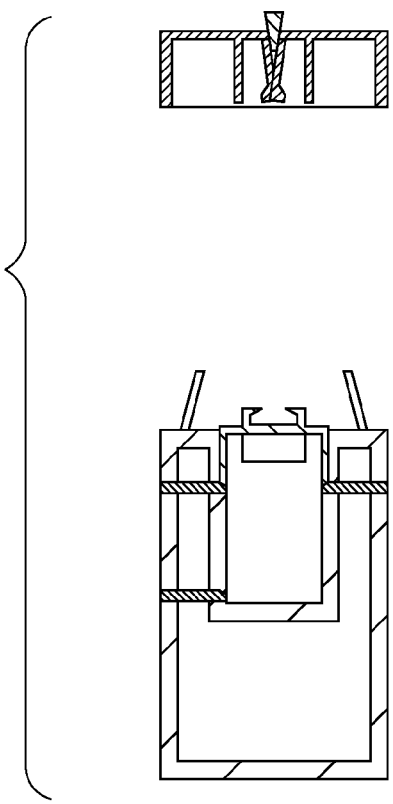

FIGS. 11A and 11B are cross-sectional views showing a liquid-discharging-cartridge fixing member 20 provided in a device body 6. FIG. 11A shows a state before the liquid-discharging-cartridge fixing member 20 operates. FIG. 11B shows a state in which the liquid-discharging-cartridge fixing member 20 operates and a liquid discharging cartridge body is fixed to the device body 6. The liquid-discharging-cartridge fixing member 20 aims to prevent a liquid discharging cartridge body 4 from deviating from its original position when a device body cap 1 combined with a discharging head cap 2 is detached from the device body 6. As shown in FIG. 11B, the liquid-discharging-cartridge fixing member 20 is operated before the device body cap 1 is attached to the device body 6. Preferably, a portion of the liquid discharging cartridge body 4 where the leading end of the liquid-discharging-cartridge fixing member 20 abuts has a recess so as to reliably fix the liquid discharging cartridge body 4. When the device body 6 is electrically controlled, operation of the liquid-discharging-cartridge fixing member 20 can be automated, similarly to the above.

To remove the liquid discharging cartridge from the device body 6 after use, the liquid-discharging-cartridge fixing member 20 is released.

FIGS. 12A to 12E are schematic views showing states in which the liquid discharging cartridge is attached to the device body 6 after the discharging head cap 2 is combined with the liquid discharging cartridge. When the user is an elderly person or a child, this method is easier than when the user attaches the liquid discharging cartridge to the device body 6 while holding the liquid discharging cartridge. Moreover, the user will not fall off the liquid discharging cartridge during attachment.

Figure 12A:
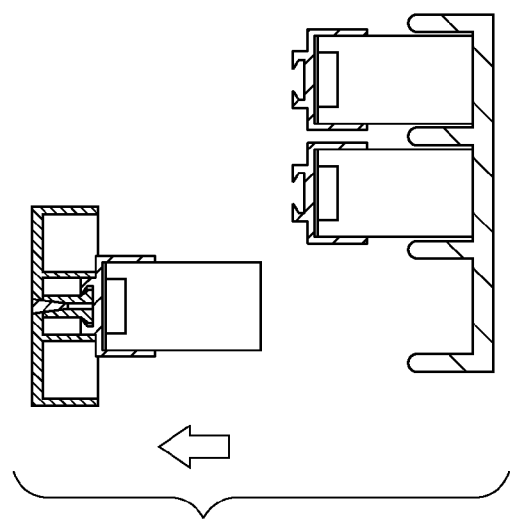
FIGS. 12A to 12E are schematic views showing a state in which a liquid discharging cartridge is set in a device body after being combined with a device body cap.
Figure 12B:
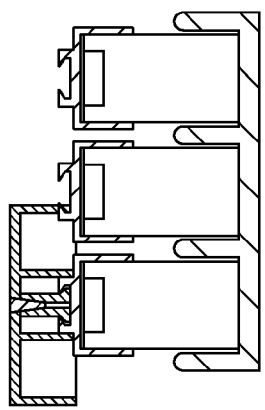
Figure 12C:
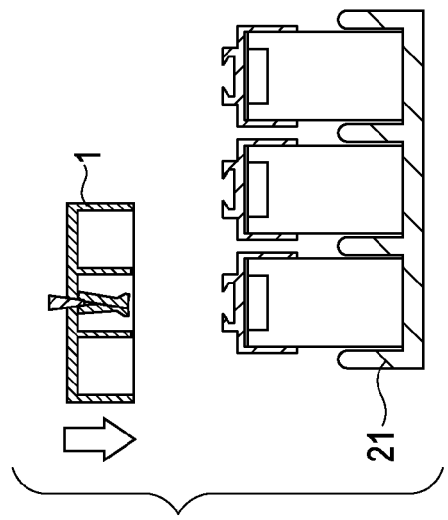
Figure 12D:
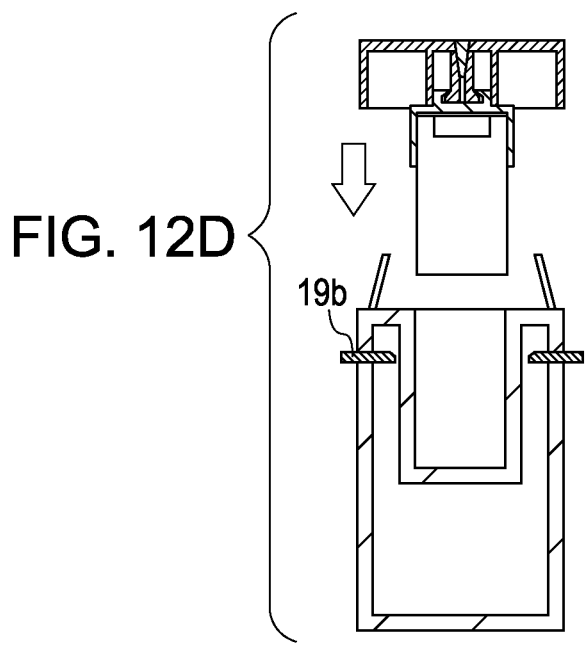
Figure 12E:
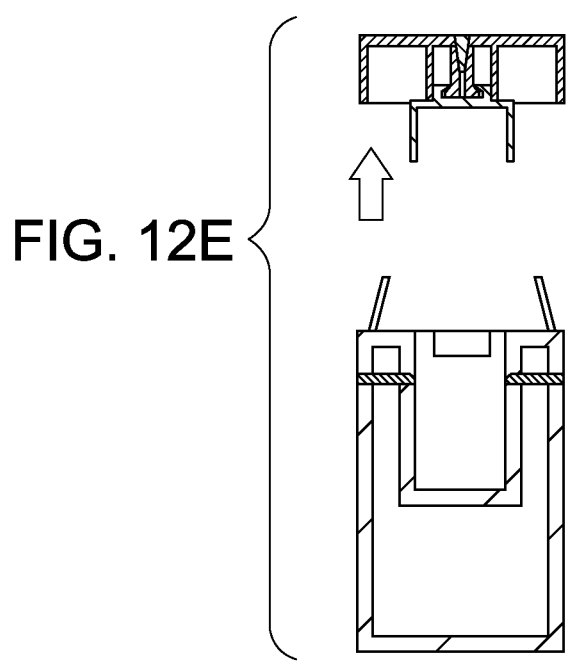

FIG. 12A shows a state before the liquid discharging cartridge set in a cartridge magazine 21 is combined with the device body cap 1. FIG. 12B shows a state in which the liquid discharging cartridge and the device body cap 1 are combined. FIG. 12C shows a state in which the combination of the device body cap 1 and the liquid discharging cartridge is removed from the cartridge magazine 21. FIG. 12D shows a state in which the combination of the device body cap 1 and the liquid discharging cartridge is attached to the device body 6. FIG. 12E shows a state in which the device body cap 1 combined with the discharging head cap 2 is detached from the device body 6 after the discharging head cap 2 is unfixed.

As described above, it is necessary to be careful not to remove the device body cap 1 combined with the discharging head cap 2 from the device body 6 before the discharging-head-cap releasing members 19b operate.

Control of Times at Which Discharging Head Cap is Unfixed and Device Body Cap is Detached (1)

In the third and fourth embodiments, the time at which the discharging head cap 2 is unfixed from the liquid discharging cartridge body 4 and the time at which the device body cap 1 and the discharging head cap 2 are combined are separate. For this reason, in a case in the unfixing time is later than the combing time, when an attempt is made to detach the device body cap 1 without performing unfixing, load may be applied to the discharging head cap 2. In the fifth embodiment, this problem is avoided by simultaneously performing unfixing and combination.

Figure 13A:
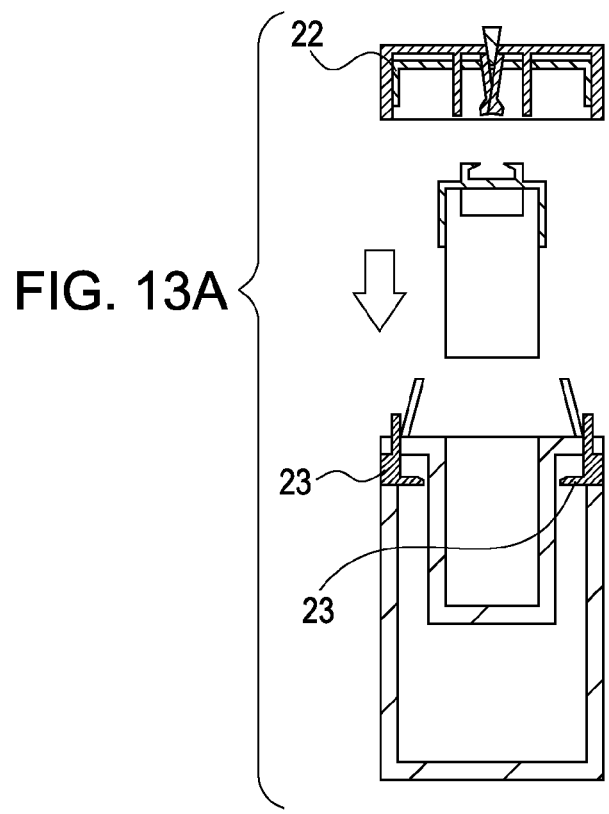
FIGS. 13A to 13E are schematic views showing a first example of a structure and a series of operations for simultaneously unfixing a discharging head cap and combining a device body cap and the discharging head cap.
Figure 13B:
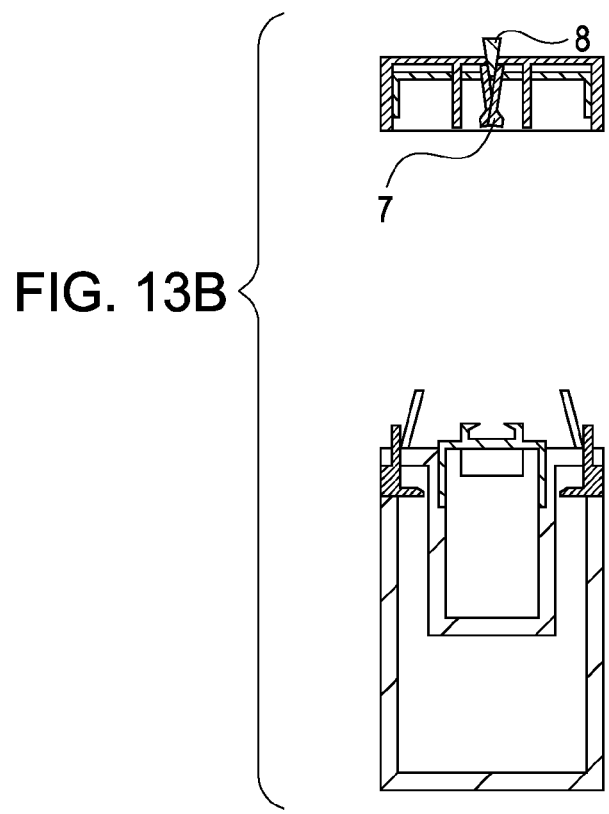
Figure 13C:
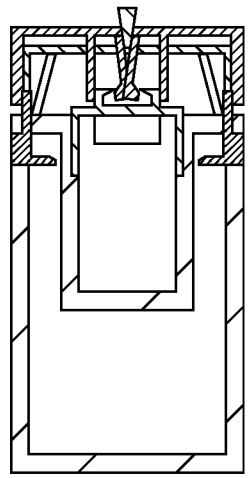
Figure 13D:
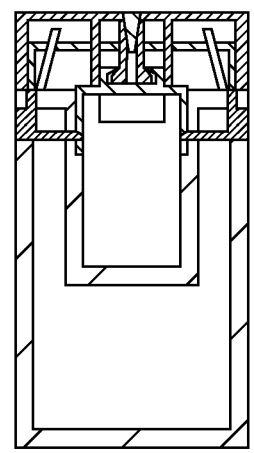
Figure 13E:
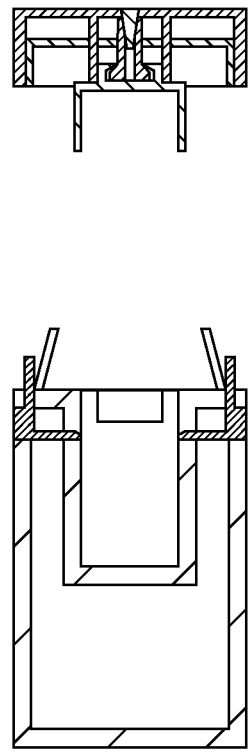

FIGS. 13A to 13E are schematic views showing a structure that allows unfixing of a discharging head cap and combination of a device body cap and the discharging head cap to be performed simultaneously, and a series of operations of the structure. FIG. 13A is a schematic view showing a state before the device body cap and a liquid discharging cartridge are combined. FIG. 13B is a schematic view showing a state in which the liquid discharging cartridge is attached to the device body. FIG. 13C is a schematic view showing a state in which the device body cap is attached to the device body. FIG. 13D is a schematic view showing a state in which force conversion type discharging-head-cap releasing members 23 and a combination operating member 8 simultaneously operate. FIG. 13E is a schematic view showing a state in which the combination of the device body cap and the discharging head cap is detached from the device body.

In the fifth embodiment, a movable hook portion 7 and a force conversion type discharging-head-cap release transmission member 22 are coupled to the combination operating member 8. When the user pushes down the combination operating member 8, the discharging-head-cap release transmission member 22 is also pushed down. This downward motion is converted into a horizontal motion by the force conversion type discharging-head-cap releasing members 23, thereby unfixing the discharging head cap. Examples of the discharging-head-cap releasing members 23 will be described with reference to FIGS. 14A to 14E.

FIGS. 14A to 14E are schematic views showing a member for unfixing the discharging head cap by changing the direction of force. FIG. 14A is a schematic view showing a method using a flexible material. FIG. 14B is a schematic view illustrating a case in which the direction of force is changed by a pantograph method. FIG. 14C is a schematic view illustrating a bow method. FIG. 14D is a schematic view illustrating a method using a rack and a pinion. FIG. 14E is a schematic view illustrating an electrical method in which a rack is moved by a motor in response to power-on.

Preferably, a flexible member 24 adopted in FIG. 14A is formed by a material that originally extends straight and returns to its original straight shape even after being bent, for example, a piano wire. Support members 25 restrict the motion of the flexible member 24. Preferably, a position recovery member 26, such as a spring, is provided so that the flexible member 24 returns to its original position when a downward force of the discharging-head-cap release transmission member 22 in the figure is removed.

In FIG. 14B, four materials are joined at their tops like a pantograph, and members 25 for restricting the motion of the joined structure so that the joined structure extends only in the horizontal direction in the figure are provided on upper and lower sides of the joined structure. It is preferable to use a position recovery member 26, similarly to the case shown in FIG. 14A. Reference numerals 28 and 29 denote a vertical-direction operating member and a horizontal-direction operating member, respectively.

In FIG. 14C, a bow-shaped member 30 in which a flexible member is bent and fixed by, for example, a thread is used. In this case, the bow-shaped member 30 itself has a position recovery property, and therefore, a position recovery member 26 is unnecessary. Reference numerals 28 and 29 denote a vertical-direction operating member and a horizontal-direction operating member, respectively.

In FIG. 14D, a vertical rack 31 is coupled to a horizontal rack 32 via a pinion gear 33. Both racks are held by support members 25 so as not to be displaced during operation. In this case, it is also preferable to use a position recovery member 26, similar to FIGS. 14A and 14B.

FIG. 14E illustrates a method that is effective when the device body 6 includes an electrical member. When the above-described discharging-head-cap release transmission member 22 is pushed down, a switch 34 is turned on, and a pinion gear 33 is rotated by a motor (not shown) to operate a horizontal rack 32. It is preferable to produce a program such as to stop the rotation of the motor after a predetermined time of operation or after the rack moves to a predetermined position.

Control of Times at Which Discharging Head Cap is Unfixed and Device Body Cap is Detached (2)

In the sixth embodiment, similarly to the fifth embodiment, the time at which a discharging head cap 2 is unfixed from a liquid discharging cartridge body 4 and the time at which a device body cap 1 and the discharging head cap 2 are combined can be the same.

FIGS. 15A to 15D are schematic views showing the sixth embodiment. In a liquid discharging cartridge body 4, two fixing rods 36a and 36b serving as discharging-head-cap fixing members and a fixing-rod driving motor 35 serving as a discharging-head-cap releasing member for performing unfixing by moving the fixing rods 36a and 36b are provided. A device body 6 includes a cartridge mounting portion 38 in which the liquid discharging cartridge body 4 is mounted, and a fixing control unit 40. The fixing control unit 40 sends, to the fixing-rod driving motor 35, a signal for unfixing a discharging head cap 2 by moving the fixing rods 36a and 36b.

Since the discharging-head-cap fixing members and the fixing control unit are thus separately provided in the discharging liquid cartridge body 4 and the device body 6, the probability that the discharging head cap 2 will be erroneously opened at an undesirable time, for example, by hand considerably decreases. This allows the surface of the discharging head 3 to be kept clean, and is desirable from the viewpoints not only of convenience but also of hygiene during inhalation of the user.

Figure 15A:
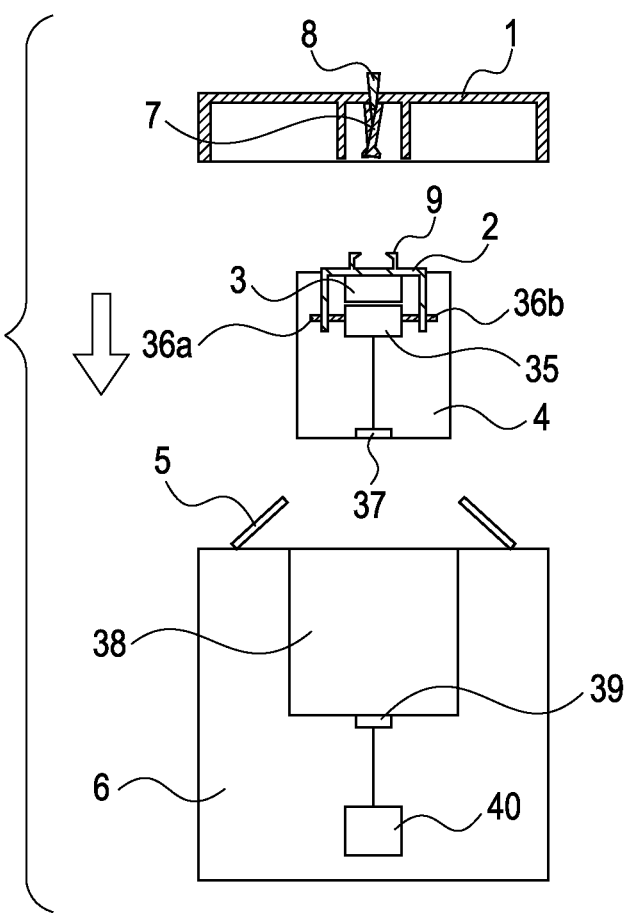
FIGS. 15A to 15D are schematic views showing a second example of a structure and a series of operations for simultaneously unfixing a discharging head cap and combining a device body cap and the discharging head cap.

To use the liquid discharging device of the embodiment, the user detaches the device body cap 1, and then attaches the liquid discharging cartridge to the device body 6 (FIG. 15A).

Figure 15B:
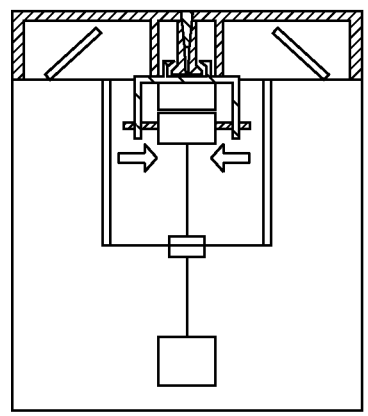

Subsequently, the user attaches the device body cap 1 to the device body 6 to combine the device body cap 1 with the discharging head cap 2. The discharging head cap 2 has a fixing hook portion 9. By pushing down a combination operating member 8 of the device body cap 1, a movable hook portion 7 opens outward to be combined with the fixed hook portion (FIG. 15B).

Figure 15C:
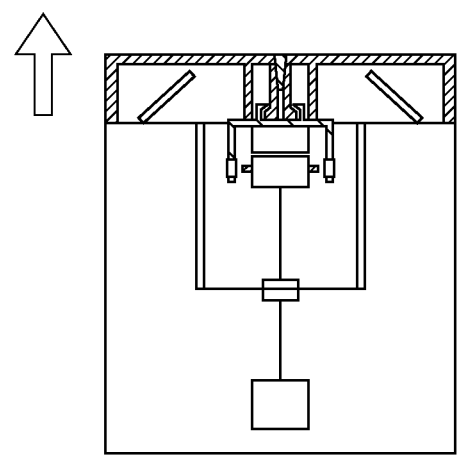

Before the user discharges the liquid, a signal is sent from the fixing control unit 40 to the fixing-rod driving motor 35 via a body-side terminal 39 and a cartridge-side terminal 37. The fixing-rod driving motor 35 moves the fixing rods 36a and 36b toward the motor 35 on the basis of the signal, whereby the discharging head cap 2 is unfixed (FIG. 15C).

Figure 15D:
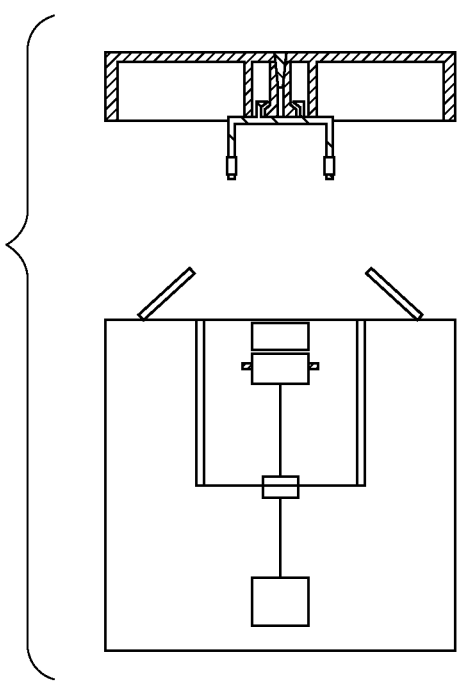

When the user detaches the device body cap 1 from the device body 6, the discharging head cap 2 is detached in combination with the device body cap 1 (FIGS. 15D and 15E). While the movable hook portion 7 is used as the coupling member in the sixth embodiment, the cap can be opened by magnetic force of a magnetic member.

Control of Times at Which Discharging Head Cap is Unfixed and Device Body Cap is Detached (3)

While the discharging-head-cap releasing member is provided in the liquid discharging cartridge and the fixing control unit is provided in the device body in the sixth embodiment, even when the arrangement is reversed, as shown in FIGS. 16A to 16D, similar advantages can be achieved.

A liquid discharging cartridge body 4 includes fixing rods 36a and 36b serving as discharging-head-cap fixing members, and a fixing control portion 43. The fixing rods 36a and 36b are formed of a magnetic material, and are respectively fixed to the liquid discharging cartridge body 4 by springs 41a and 41b. On the other hand, a device body 6 includes electromagnets 42a and 42b serving as discharging-head-cap releasing members for unfixing the fixing rods 36a and 36b formed of the magnetic material.

Figure 16A:
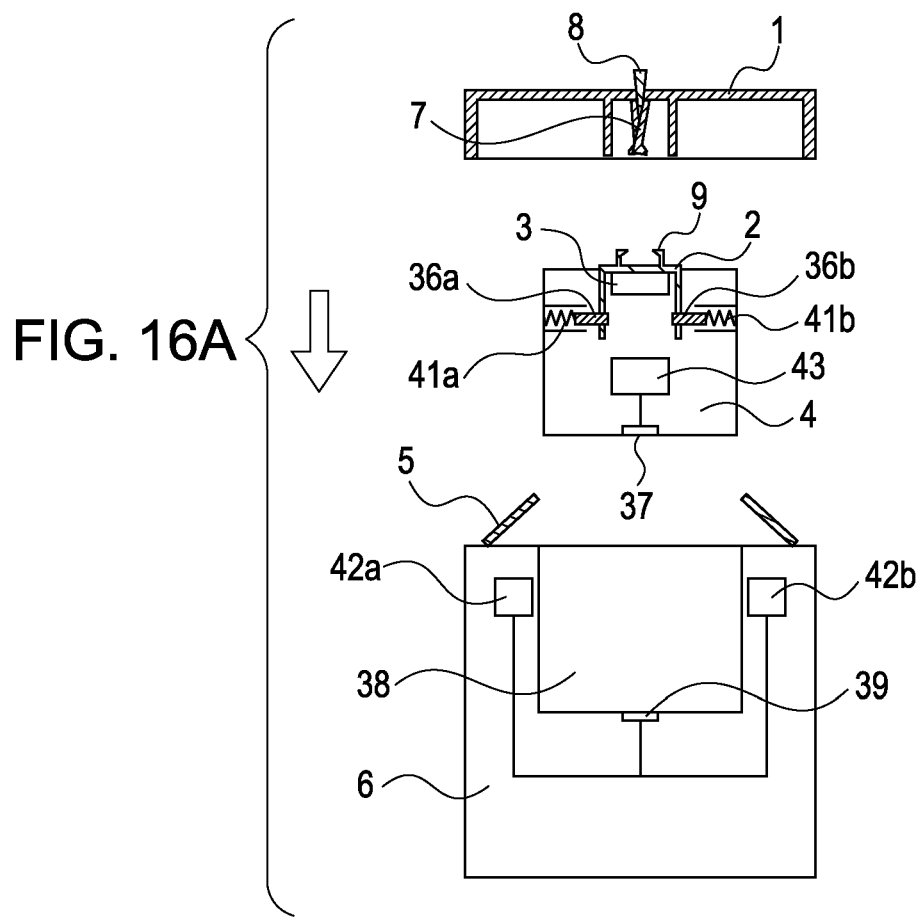
FIGS. 16A to 16D are schematic views showing a third example of a structure and a series of operations for simultaneously unfixing a discharging head cap and combining a device body cap and the discharging head cap.

To use the liquid discharging device of the embodiment, the user detaches a device body cap 1, and then attaches a liquid discharging cartridge to the device body 6 (FIG. 16A).

Figure 16B:
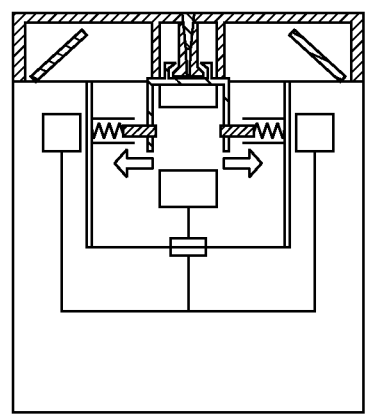

Subsequently, the user attaches the device body cap 1 to the device body 6 to combine the device body cap 1 with a discharging head cap 2 having a fixed hook portion 9. By pushing down a combination operating member 8 of the device body cap 1, a movable hook portion 7 opens outward to be combined with the fixed hook portion 9 (FIG. 16B).

Figure 16C:
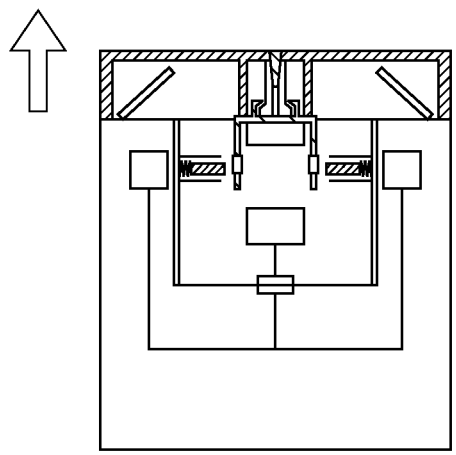

Before the user discharges liquid, a signal is sent from the fixing control unit 43 to the electromagnets 42a and 42b via a cartridge-side terminal 37 and a body-side terminal 39. The electromagnets 42a and 42b move the fixing rods 36a and 36b toward the device body 6 on the basis of the signal, whereby the discharging head cap 2 is unfixed (FIG. 16C).

Figure 16D:
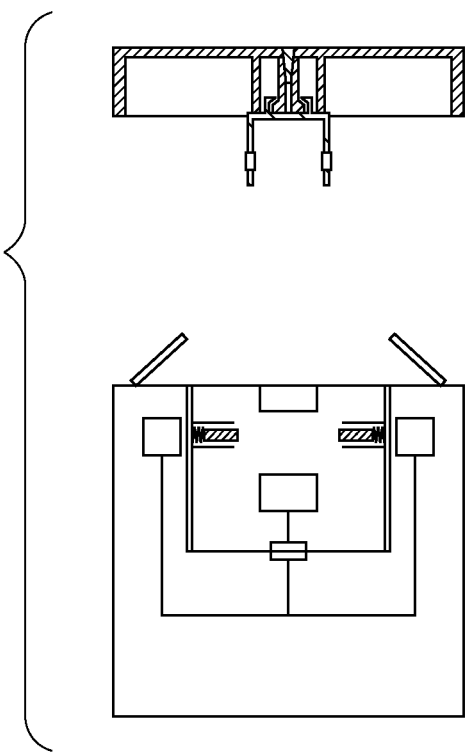

When the user detaches the device body cap 1 from the device body 6, the discharging head cap 2 is detached in combination with the device body cap 1 (FIG. 16D).

While the electromagnets are used as the discharging-head-cap releasing members in the seventh embodiment, fixing rods formed of a non-insulating material may be moved in a non-contact manner by electrostatic force obtained by applying voltage to discharging-head-cap releasing members formed of an insulating material. However, from the viewpoint of the volume of force to be generated, it is preferable to use electromagnets.

Control of Times at Which Discharging Head Cap is Unfixed and Device Body Cap is Detached (4)

In the sixth and seventh embodiments, the liquid discharging cartridge includes the discharging-head-cap releasing member 35 or the fixing control unit 43. Alternatively, when a discharging-head-cap releasing member and a fixing control unit are provided in the device body and a discharging-head-cap fixing member is provided in the liquid discharging cartridge body, as shown in FIGS. 17A to 17D, hygienic advantages can be obtained similarly to the above.

Figure 17A:
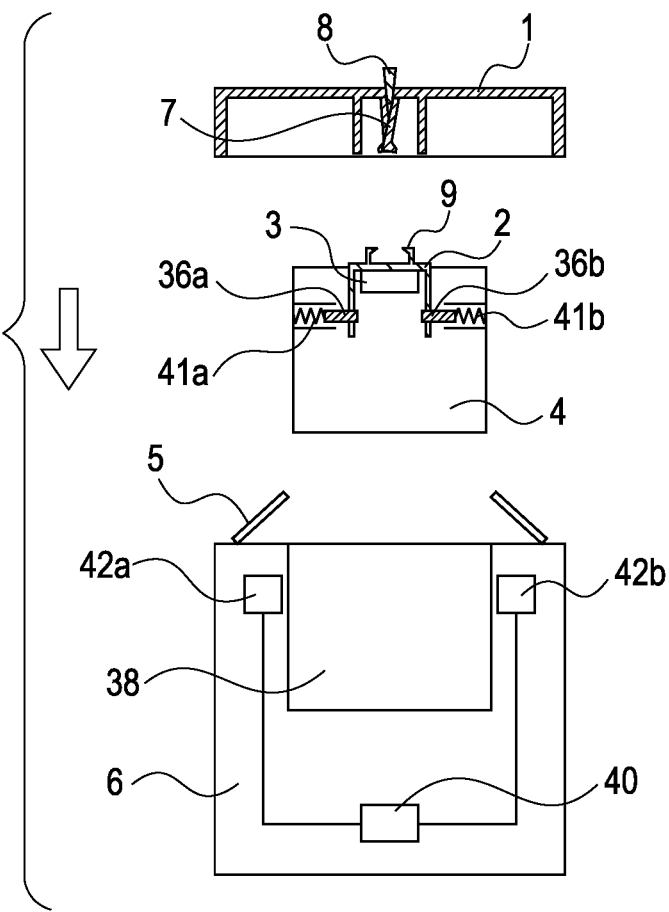
FIGS. 17A to 17D are schematic views showing a fourth example of a structure and a series of operations for simultaneously unfixing a discharging head cap and combining a device body cap and the discharging head cap.

To use the liquid discharging device of the embodiment, the user detaches a device body cap 1, and attaches a liquid discharging cartridge to a device body 6 (FIG. 17A).

Figure 17B:
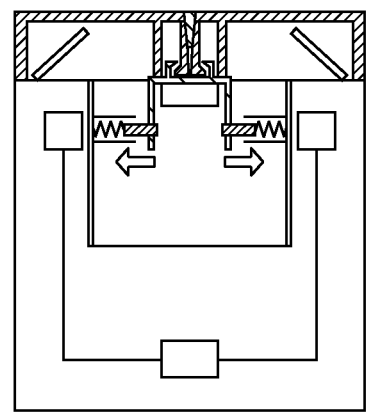

Subsequently, the user attaches the device body cap 1 to the device body 6 to combine the device body cap 1 with a discharging head cap 2 having a fixed hook portion 9. By pushing down a combination operating member 8 of the device body cap 1, a movable hook portion 7 opens outward to be combined with the fixed hook portion 9 (FIG. 17B).

Figure 17C:
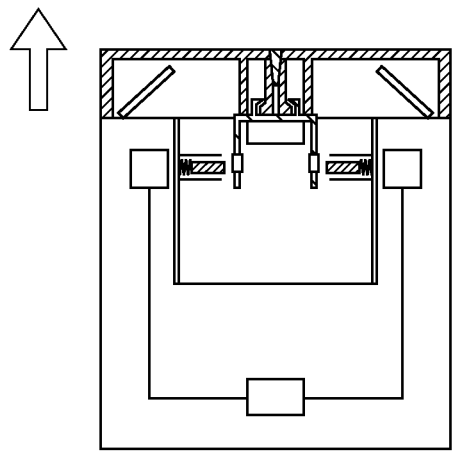

Before the user discharges liquid, a signal is sent from a fixing control unit 40 to electromagnets 42a and 42b. The electromagnets 42a and 42b move fixing rods 36a and 36b toward the device body 6 on the basis of this signal, whereby the discharging head cap 2 is unfixed (FIG. 17C).

Figure 17D:
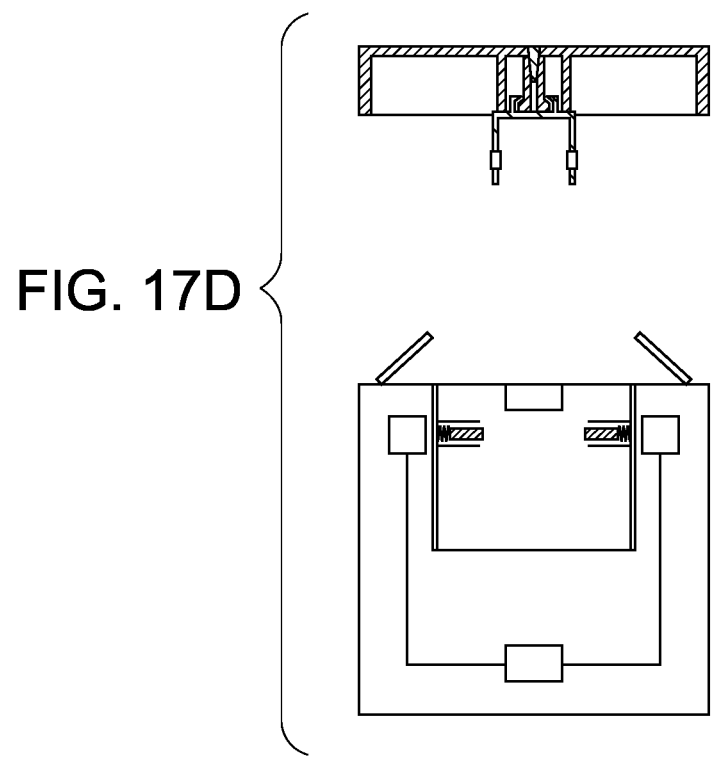

When the user detaches the device body cap 1 from the device body 6, the discharging head cap 2 is detached in combination with the device body cap 1 (FIG. 17D). Since the liquid discharging cartridge is replaced according to the amount of remaining liquid, it is preferable, in terms of cost, that the discharging-head-cap releasing member and the fixing control unit be provided in the device body.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-286729 filed Nov. 7, 2008, which is hereby incorporated by reference herein in its entirety.

What is claimed is:

1. A liquid discharging device comprising:
   a device body configured to house a liquid discharging cartridge body having a liquid discharging portion that discharges liquid;
   a device body cap removably attached to the device body; and
   a coupling member configured to couple the device body cap to a discharging portion cap attached to the liquid discharging cartridge body so as to protect a discharging port of the liquid discharging portion,
   wherein the coupling member causes the discharging portion cap to be detached from the liquid discharging portion when the device body cap is detached from the device body.

2. The liquid discharging device according to claim 1, further comprising:
   a switch member configured to switch the coupling member between a coupled state in which the device body cap and the discharging portion cap are coupled and an uncoupled state in which the device body cap and the discharging portion cap are not coupled.

3. The liquid discharging device according to claim 1, further comprising:
a fixing member configured to fix the discharging portion cap to the liquid discharging cartridge body.

4. The liquid discharging device according to claim 3, further comprising:
a control unit configured to release fixing of the discharging portion cap and the liquid discharging cartridge body by the fixing member.

5. A liquid discharging cartridge comprising:
a liquid discharging portion configured to discharge liquid; and
a discharging portion cap configured to protect a discharging port of the liquid discharging portion,
wherein the discharging portion cap includes a coupling member to be coupled to a device body cap provided in and detachable from a device body of a liquid discharging device that houses the liquid discharging cartridge, and
wherein the coupling member causes the discharging portion cap to be detached from the liquid discharging portion when the device body cap is detached from the device body.

6. The liquid discharging cartridge according to claim 5, further comprising:
a switch member configured to switch the coupling member between a coupled state in which the device body cap and the discharging portion cap are coupled and an uncoupled state in which the device body cap and the discharging portion cap are not coupled.

7. The liquid discharging cartridge according to claim 5, further comprising:
a fixing member configured to fix the discharging portion cap to the liquid discharging cartridge.

8. A device body cap removably attached to a device body of a liquid discharging device that houses a liquid discharging cartridge body having a liquid discharging portion for discharging liquid, the device body cap comprising:
a coupling member to be coupled to a discharging portion cap provided in the liquid discharging cartridge body so as to protect a discharging port of the liquid discharging portion,
wherein the coupling member causes the discharging portion cap to be detached from the liquid discharging portion when the device body cap is detached from the device body.

9. The device body cap according to claim 8, further comprising:
a switch member configured to switch the coupling member between a coupled state in which the device body cap and the discharging portion cap are coupled and an uncoupled state in which the device body cap and the discharging portion cap are not coupled.

* * * * *